United States Patent [19]

Sarama

[11] Patent Number: 5,559,226
[45] Date of Patent: Sep. 24, 1996

[54] PROCESS FOR MAKING POLYOL FATTY ACID POLYESTERS HAVING OXIDATIVE STABILITY

[75] Inventor: Robert J. Sarama, Loveland, Ohio

[73] Assignee: The Procter & Gamble Company, Cincinnati, Ohio

[21] Appl. No.: 215,403

[22] Filed: Mar. 21, 1994

Related U.S. Application Data

[63] Continuation of Ser. No. 993,492, Dec. 18, 1992, abandoned, which is a continuation of Ser. No. 685,419, Apr. 12, 1991, abandoned.

[51] Int. Cl.$^6$ ............................. C07H 1/06; C07H 13/02
[52] U.S. Cl. ........................ 536/115; 536/116; 536/119; 536/124; 536/127
[58] Field of Search ............................. 536/119, 115, 536/116, 124, 127

[56] References Cited

U.S. PATENT DOCUMENTS

| | | | |
|---|---|---|---|
| 2,893,990 | 7/1959 | Hass et al. | 536/119 |
| 3,198,784 | 8/1965 | Griscom et al. | 536/119 |
| 3,251,827 | 5/1966 | Schnell et al. | 536/119 |
| 3,558,597 | 1/1971 | Brachel et al. | 536/119 |
| 3,644,333 | 2/1972 | Osipow et al. | 536/119 |
| 3,792,041 | 2/1974 | Yamagishi et al. | 536/119 |
| 3,849,341 | 11/1974 | Lamberti | 536/115 |
| 3,963,699 | 6/1976 | Rizzi et al. | 536/119 |
| 4,032,702 | 6/1977 | James | 536/119 |
| 4,298,730 | 11/1981 | Galleymore et al. | 536/119 |
| 4,334,061 | 6/1982 | Bossier et al. | 536/115 |
| 4,517,360 | 5/1985 | Volpenhein | 536/119 |
| 4,518,772 | 5/1985 | Volpenhein | 523/135 |
| 4,877,871 | 10/1989 | Klemann et al. | 536/124 |
| 4,931,552 | 6/1990 | Gibson et al. | 536/124 |
| 4,942,228 | 7/1990 | Gibson | 536/119 |
| 4,952,687 | 8/1990 | Bodor et al. | 514/23 |
| 4,973,681 | 11/1990 | Watanabe | 536/119 |
| 5,055,571 | 10/1991 | Van Lookeren | 536/119 |

FOREIGN PATENT DOCUMENTS

| | | | |
|---|---|---|---|
| 319091 | 6/1989 | European Pat. Off. | |
| 319092 | 6/1989 | European Pat. Off. | |
| 424066 | 4/1991 | European Pat. Off. | C07H 13/06 |
| 434119 | 6/1991 | European Pat. Off. | C07H 13/06 |
| 434117 | 6/1991 | European Pat. Off. | C07H 13/06 |
| 91/15960 | 10/1991 | WIPO | A23D 7/00 |
| 92/04360 | 3/1992 | WIPO | C07H 13/06 |

OTHER PUBLICATIONS

Ungerman et al., Effects of Bleaching on Oil Oxidative Properties, Harshaw/Filtrol (CA), AOCS Annual Meeting, Phoenix, AZ, May 11, 1988.
Engelhard, Material Safety Data Sheet, Grade F–105 (Code J96820) printed Aug. 24, 1994, dated Jul. 19, 1993.
Hastert, Effective Adsorptive Treatment of Edible Oils, AOCS Short Course, Phoenix, AZ., May 4–7, 1988.
Engelhard, Fats & Oils Catalysts, rev. Jul. 27, 1994.
Buck, Daniel F., Antioxidant Applications, Manufacturing Confectioners Association Production Conference, 1985.
Hendrix, World Conference Proceedings, Edible Fats and Oil Processing, American Oil Chemists Society, pp. 94–100; 1990.
Cowan, J. C., Degumming, Refining, Bleaching and Deodorization Theory, 53 Journal of American Oil Chemists Society, Jun. 1976.
Try Sil Alkaline silica, mfd. by W. R. Grace, P.O. Box 2117, Baltimore, MD, 1989.
Pure–Flo, mfd. by Oil Dri Corp. of America, 520 N. Michigan Ave., Chicago, IL, 1990.
Filtrol 105, mfd. by Engelhard Corp., Catalyst and Chemicals Div., Jackson, MS Bulletin on Filtrol Grade 105, published by Harshaw/Filtrol (1988).
Erickson, D. R., World Conference Proceedings, Edible Fats and Oil Processing, American Oil Chemists Society, "Chemical and Physical Properties of Solvents Considered for Extraction of Edible Oils (38)", pp. 65–67 (1990).
A.O.C.S. Official Method Cd 12–57, "Fat Stability", Reapproved 1989.

*Primary Examiner*—Douglas W. Robinson
*Assistant Examiner*—Everett White
*Attorney, Agent, or Firm*—John M. Howell; Tara M. Rosnell; Rose Ann Dabek

[57] ABSTRACT

Polyol fatty acid polyesters having improved oxidative stability are prepared using the addition of an alkaline material to the synthesized crude polyol fatty acid polyesters before conducting the finishing of the crude. The alkaline material is added in an amount such that the finished product has a pH of from about 6.0 to about 8.5.

29 Claims, 1 Drawing Sheet

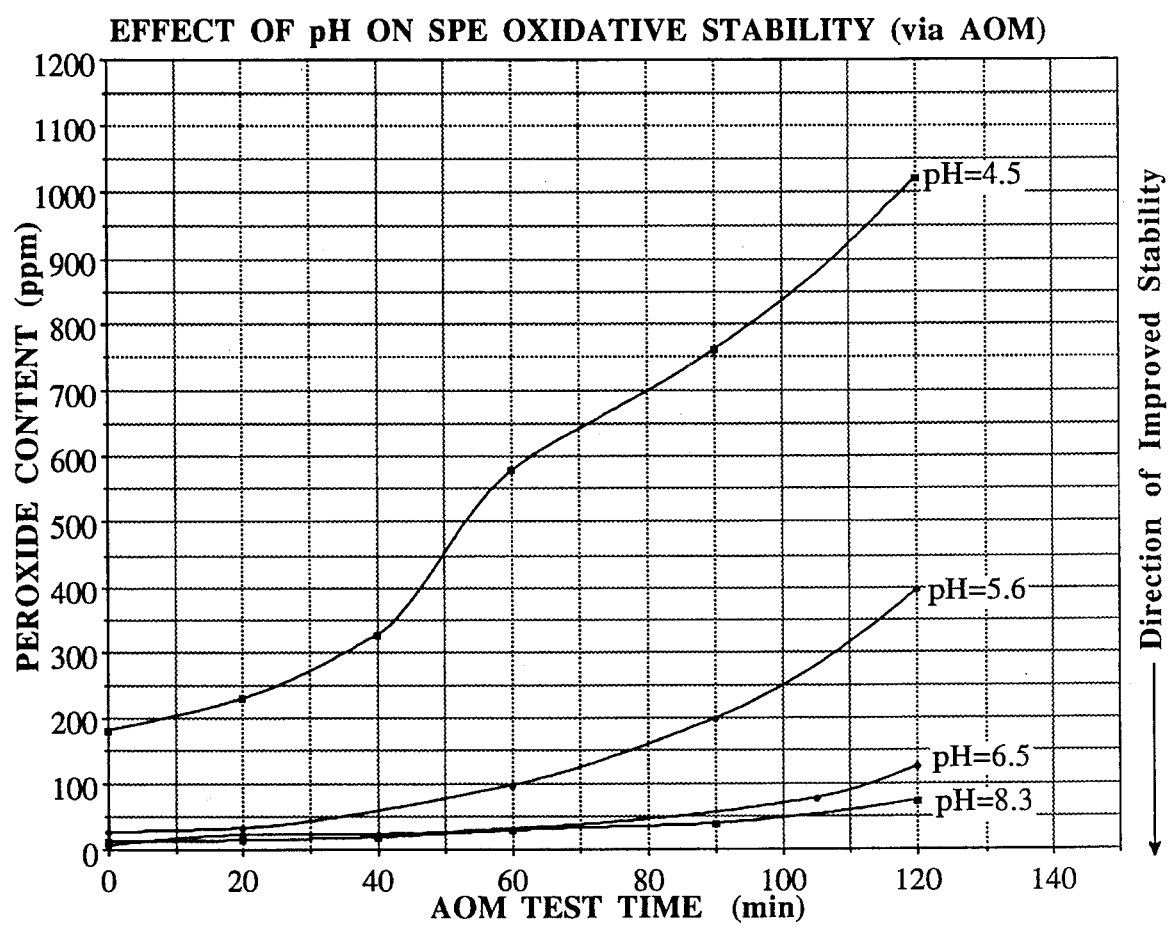

PROCESS FOR MAKING POLYOL FATTY ACID POLYESTERS HAVING OXIDATIVE STABILITY

This is a continuation of application Ser. No. 07/993,492, filed on Dec. 18, 1992, now abandoned, which is a continuation of application Ser. No. 07/685,419, filed Apr. 12, 1991, now abandoned.

TECHNICAL FIELD

This invention relates to a process for making polyol fatty acid polyesters, especially sucrose polyesters, having improved oxidative stability.

BACKGROUND OF THE INVENTION

Processes for preparing polyol fatty acid polyesters, including processes that utilize solvent-free transesterification reactions, have been described in U.S. Pat. No. 3,963,699, Rizzi et al., issued Jun. 15, 1976; U.S. Pat. No. 4,517,360, Volpenhein, issued May 14, 1985; and U.S. Pat. No. 4,518,772, Volpenhein, issued May 21, 1985. Additional patents describing processes for preparing lower and higher esters of polyols include U.S. Pat. No. 2,893,990, Hass et al., issued Jul. 7, 1959; U.S. Pat. No. 3,251,827, Schnell et al., issued May 17, 1966, which discloses that the particle size of the sugar should be kept small to avoid formation of higher esters; U.S. Pat. No. 3,558,597, Brachel et al., issued Jan. 26, 1971; U.S. Pat. No. 3,644,333, Osipow et al., issued Feb. 22, 1972; U.S. Pat. No. 3,792,041, Yamagishi et al., issued Feb. 12, 1974, all which disclose making a solution of sucrose and fatty acid soap in water and adding the fatty acid ester and catalyst before elevating the temperature to drive off the water; U.S. Pat. No. 4,032,702, James, issued Jun. 28, 1977, which discloses using lower esters of sucrose as emulsifiers in the preparation of lower esters and the use of soap as a catalyst for such reactions; U.S. Pat. No. 4,298,730, Galleymore et al., issued Nov. 3, 1981, which also discloses the use of soap as an emulsifier and catalyst; U.S. Pat. No. 4,334,061, Bossier et al., issued Jun. 8, 1982, which discloses the use of a water washing step to purify the polyol polyester and incidentally discloses the use of inert gas sparging to remove lower alcohol from the reaction between sucrose and lower alkyl ester of fatty acid to speed the reaction and the removal of unreacted sucrose from an initial stage of a batch reaction for no indicated reason; and U.S. Pat. No. 4,877,871, Klemann et al., issued Oct. 31, 1989. All of said above patents are incorporated herein by reference.

Many of the above patents teach processes that use solvents to assist in the formation of a homogeneous reaction mixture. However, the solvent must ultimately be removed before the polyester can be ingested. Also, many of the processes involving solvents are primarily for preparation of esters having only a low degree of esterification, i.e. containing one or two ester groups, that are useful as surfactants.

Using alkaline materials in the process for making polyol fatty acid polyesters is known in the art. For example, U.S. Pat. No. 3,198,784, Griscom et al., issued Aug. 3, 1965, discloses adding sodium hydroxide to an aqueous solutions of sucrose as a preliminary step for making benzylated sucrose. U.S. Pat. No. 3,849,3412, Lamberti, issued Nov. 19, 1974 discloses using alkaline solutions for making ester-linked derivatives of carbohydrates. European Patent Applications 319,091 and 319,092, both assigned to Unilever and published Jun. 7, 1989, disclose methods for making light color, polyol fatty acid oils by utilizing alkaline solutions in the purification steps.

European patent application 319,092 discloses rinsing the crude polyol polyesters with an alkaline solution, having a pH of at least 12.5, at temperatures from 40° C.–110° C. European patent application 319,091 discloses a process for lowering the level of residual alkali metal ions left over from the base catalyzed synthesis and/or the purification proceedure disclosed in European patent application 319,092. The process is aimed at reducing the level of alkali metals in the polyol fatty acid ester to no more than 5 ppm by weight of the finished product. Although the light colored, polyol fatty acid polyester oils made therein are reported to have improved keepability, no improved oxidative stability of said oils is disclosed.

The present invention relates to processes for making polyol fatty acid polyesters having improved oxidative stability. These polyol fatty acid polyesters may be used, for example, to make cooking oils having superior flavor and odor, longer shelf-life, and longer fryer-life.

SUMMARY OF THE INVENTION

The improved process of the present invention comprises the step of adding an alkaline material to the crude polyol fatty acid polyester after synthesis, but prior to the finishing of the crude product. The alkaline material is added to the crude polyol fatty acid polyester in an amount such that the pH level of the finished polyol fatty acid polyester is from about 6.0 to about 8.5.

DESCRIPTION OF THE DRAWING

The drawing herein is a graph comparing the oxidative stability of sucrose polyesters made using the present inventive process with sucrose polyesters which are not.

DETAILED DESCRIPTION OF THE INVENTION

The present invention is for a process for making polyol fatty acid polyesters having improved oxidative stability. This improvement is realized by utilizing an additional step comprising adding an alkaline material to the crude polyol fatty acid polyester at a point in the process after synthesis, but before the finishing of the crude product. The alkaline material is added in an amount sufficient to provide a finished product pH of from about 6 to about 8.5, when measured at 110° F.–120° F. in a 10% solution of polyol fatty acid polyester in neutral deionized water, isopropyl alcohol, and mixtures thereof.

As stated above, the alkaline material is added after the synthesis, but before the finishing stage of the manufacturing process. This is usually done at a point no later than the removal of the residual ester reactant from the crude product. For example, when synthesizing sucrose polyesters with methyl esters, the alkaline material is added before removal of the residual methyl ester from the crude synthesized product.

When the alkaline material is added at another point in the process (e.g. during the water washing steps as disclosed in European patent application 319,0920), no significant improvement in the oxidative stability of the polyol fatty acid polyesters is realized. Although not wishing to be limited by theory, it is believed that adding the alkaline material at the above disclosed point in the process deters the formation of pro-oxidants from minor components in the crude product mixture. This is surprising since it is known in the art that alkaline conditions promote free radical oxidation; see Buck, Daniel F., "Antioxidant Applications", *The Manufacturing Confectioner Assoc. Production Conference,* 1985, herein incorporated by reference. Minimization of pro-oxidants during the refining and finishing steps of the manufacturing process yields polyol fatty acid polyesters with improved flavor and odor, longer shelf-life.

In summary, products made using the polyol fatty acid is polyesters made by the present process maintain good flavor and odor over longer periods of storage and use.

The following is a general disclosure of the process for manufacturing such polyol fatty acid polyesters, particularly sucrose fatty acid polyesters.

A. Polyol Fatty Acid Polyesters

As used herein, the term "polyol" is intended to include any aliphatic or aromatic compound containing at least four free hydroxyl groups. In practicing the process disclosed herein, the selection of a suitable polyol is simply a matter of choice. For example, suitable polyols can be selected from the following classes: saturated and unsaturated straight and branched chain linear aliphatics; saturated and unsaturated cyclic aliphatics, including heterocyclic aliphatics; or mononuclear or polynuclear aromatics, including heterocyclic aromatics. Carbohydrates and nontoxic glycols are preferred polyols. Monosaccharides suitable for use herein include, for example, mannose, galactose, arabinose, xylose, ribose, apiose, rhamnose, psicose, fructose, sorbose, tagitose, ribulose, xylulose, and erythrulose. Oligosaccharides suitable for use herein include, for example, maltose, kojibiose, nigerose, cellobiose, lactose, melibiose, gentiobiose, turanose, rutinose, trehalose, sucrose and raffinose. Polysaccharides suitable for use herein include, for example, amylose, glycogen, cellulose, chitin, inulin, agarose, zylans, mannan and galactans. Although sugar alcohols are not carbohydrates in a strict sense, the naturally occurring sugar alcohols are so closely related to the carbohydrates that they are also preferred for use herein. The sugar alcohols most widely distributed in nature and suitable for use herein are sorbitol, mannitol and galactitol. It is desirable that the aldehyde groups be changed to alcohol groups or reacted with alcohol groups to form ether linkages. E.g., the polyol can be an alkyl glycoside or polyglycoside, especially glucosides and polyglucosides.

Particularly preferred classes of materials suitable for use herein include the monosaccharides, the disaccharides and sugar is alcohols. Preferred carbohydrates and sugar alcohols include xylitol, sorbitol and sucrose. The most preferred is sucrose.

As used herein, the term "fatty acid esters" is intended to include the $C_1$–$C_4$ (preferably methyl), 2-methoxy ethyl and benzyl esters of fatty acids containing about eight or more carbon atoms, and mixtures of such esters. Suitable reactant esters can be prepared by the reaction of diazoalkanes and fatty acids, or derived by alcoholysis from the fatty acids naturally occurring in fats and oils. Suitable fatty acid esters can be derived from either synthetic or natural, saturated or unsaturated fatty acids and include positional and geometrical isomers. Suitable preferred saturated fatty acids include, for example, caprylic, capric, lauric, myristic, palmitic, stearic, behenic, isomyristic, isomargaric, and anteisoarachadic. Suitable preferred unsaturated fatty acids include, for example, myristoleic, palmitoleic, ricinoleic, linoleic, oleic, elaidic, linolenic, eleostearic, arachidic, arachidonic, erucic, and erythrogenic acids. Mixtures of fatty acids derived from soybean, palm, safflower, rapeseed, canola, peanut, sunflower, cottonseed and/or corn oils are especially preferred for use herein. For example, rapeseed provides a good source for $C_{22}$ fatty acid. $C_{16}$–$C_{18}$ fatty acid can be provided by tallow, soybean oil, or cottonseed oil. Shorter chain fatty acids can be provided by coconut, palm kernel, or babassu oils. Corn oil, lard, olive oil, palm oil, peanut oil, safflower seed oil, sesame seed oil, and sunflower seed oil, are examples of other natural oils which can serve as the source of the fatty acid component.

Alkali metal soaps are typically used in the processes for preparing polyol polyesters of the types described herein. As used herein, the term "alkali metal fatty acid soap" is intended to include the alkali metal salts of saturated and unsaturated fatty acids having from about 8 to about 18 carbon atoms. Accordingly, suitable alkali metal fatty acid soaps include, for example, the lithium, sodium, potassium, rubidium, and cesium salts of the fatty acids described hereinbefore, especially saturated fatty acids such as capric, lauric, myristic, palmitic, and stearic acids, as well as mixtures thereof. Palmitic and stearic are preferred. Mixtures of fatty acids derived from soybean oil, palm, peanuts, canola, cottonseed, sunflower oil, safflower oil, and/or corn oil are preferred for use herein. Accordingly, preferred alkali metal fatty acid soaps include, for example, the potassium soap made from soybean oil fatty acids. The essentially fully hydrogenated materials, e.g., I.V. of less than about 8, preferably less than about 2 are especially preferred.

In a preferred process of preparing polyesters of sucrose especially utilizing the methyl esters of soybean oil fatty acids, it is highly desirably to have present an alkali metal, e.g., potassium or sodium, salt of saturated fatty acids containing from about 16 to about 22 carbon atoms. Intimate mixture of the very finely divided ingredients is important to achieving a good reaction.

The basic catalysts generally suitable for use in preparing the polyol polyesters described herein are those selected from the group consisting of alkali metals, such as aluminum, sodium, lithium and potassium: alloys of two or more alkali metals, such as sodium-lithium and sodium-potassium alloys; alkali metal hydrides, such as sodium, lithium and potassium hydride; and alkali metal alkoxides, such as potassium t-butoxide and sodium methoxide. The use of these catalysts is further taught in U.S. Pat. No. 4,517,360, Volpenhein, issued May 14, 1985, incorporated herein by reference.

More reactive catalysts such as potassium or sodium methoxide should be protected until their addition into the reaction mixture. Preferably the catalyst should be suspended in, or more preferably encapsulated by, a material that will either be present in the reaction mixture or be readily separated from the reaction mixture. Suitable encapsulating agents include said alkyl esters of, e.g., $C_{16}$–$C_{22}$ fatty acids. Addition of these more alkaline, reactive catalysts in the later stages after the polyol has an average degree of esterification of more than about 60%, preferably more than about 85%, can provide improved reaction kinetics and result in a greater degree of esterification of the polyol yet does not create the level of color/odor materials that would be created if such catalysts are present from the start of the reaction.

B. Synthesis of Polyol Fatty Acid Polyesters

In general, by way of example, an initial heterogeneous reaction mixture comprises from about 10% to about 30%, preferably from about 14% to about 18%, by weight of polyol; from about 60% to about 90%, preferably from about 70% to about 80%, by weight of the fatty acid esters; from about 0.1% to about 20%, preferably from about 0.2% to about 10%, by weight of the emulsifier, e.g., alkali metal fatty acid soap; and from about 0.1% to about 3%, preferably from about 0.1% to about 1%, by weight of basic catalyst component. In general it is desirable, and even preferred, to effect the reaction in at least two steps. In any later step, additional fatty acid esters and, optionally, more basic catalyst are added. In any second, or later step, fatty acid esters are added to raise the ratio of fatty acyl groups, i.e. fatty acid groups, to polyols above the theoretical, fully esterified, levels of at least about 25%, or preferably by at least 50%, over the theoretical level. The catalyst in the initial step can be potassium carbonate as described hereinbefore or an alkali metal hydroxide at low levels. In any later step, the catalyst can be either the same as the initial catalyst or can be a different catalyst such as potassium or sodium methoxide.

The reaction mixture is typically heated to a temperature within the range from about 194° F. (90° C.) to about 325° F. (163° C.), preferably from about 266° F. (130° C.) to about 284° F. (140° C.), under a pressure of from about 0.1 mm Hg to about 760 mm Hg. It is highly preferred that the reaction mixture, or mixtures, be agitated (e.g. stirred) as vigorously as possible. The temperature in subsequent stages is from about 175° F. (80° C.) to about 275° F. (135° C.), preferably from about 210° F. (99° C.) to about 250° F. (121° C.), as discussed hereinbefore. The mixing is increased in the subsequent stages by the preferred step of sparging with an inert gas, preferably nitrogen, carbon dioxide, low molecular weight hydrocarbons, oxides of nitrogen, etc. With sparging, the removal of volatile alcohol produced in the reaction is promoted and the reaction is speeded up so that the temperature can be kept low and/or the pressure can be kept higher. Low temperatures in the subsequent later stages are highly desirable to minimize the formation of unwanted by-products including di-fatty ketones/beta-ketoesters, other carbonyl compounds, ring structures, etc.

C. Refining and Finishing The Crude Product

After the reaction has reached the desired state of completion, the catalyst, the residual fatty ester reactant, and any emulsifier (soap), are removed since they should not be consumed along with the final polyol fatty acid polyesters. This removal is accomplished during the refining and finishing stage of polyol fatty acid polyester manufacture:

1. Refining of the polyol fatty acid polyesters comprises removing the soap and catalyst from the crude product. Similar refining steps are disclosed in Erickson, D. R., World Conference Proceedings, "Edible Fats and Oils Processing", *American Oil Chemists Soc.*, 1990; herein incorporated by reference. Most refining methods primarily involve adding water to the crude polyol fatty acid polyester, and subsequently removing it by centrifuging the mixture. This method is effective for removing soap and catalyst. The level of water added to the crude polyol fatty acid polyester is from about one half to about ten times the amount of soap removed by the method. However, even after centrifuging, the reaction mixture can still contain an undesirable level of residual soap and/or color bodies. Therefore, it is useful to repeat the water washing step followed by gravity or centrifugal separation of the aqueous phase.

A subsequent refining step involves a vacuum drying and adsorptive bleaching operation. This step can be used in combination with, or in place of, the second washing step above. Adsorbents such as bleaching earth, silica gel, and activated charcoal are typically used in drying and/or adsorptive bleaching operations of edible oils. The adsorbents are preferably added at a level of from about 0.1% to about 10% by weight of the dry reaction mixture. After the bleaching operation, the adsorbents are removed from the reaction mixture by filtration. The second stage water washing, and/or drying, and/or adsorptive bleaching completes the removal of soap and color bodies.

2. Finishing of the polyol fatty acid polyesters comprises removing unwanted materials, such as free fatty acids, excess fatty acid ester reactant, and negative flavor components. Typical fatty acid removal is disclosed in Cowan, J. C., Degumming, Refining, Bleaching, and Deodorization Theory, 53 *Journal of American Oil Chemists Soc.*, June 1976; herein incorporated by reference. The finishing steps used in the present invention include thermal evaporation, high temperature steam distillation, and combinations thereof:

(a) Thermal evaporation comprises heating the polyol polyester crude to a temperature equivalent to the unwanted material's bubble point at evaporator pressure. The crude is fed into a thermal evaporator, such as agitated film, wiped film, flash, rising film, or falling film evaporator, wherein the crude is heated to a temperature of about 380° F. (190° C.) to about 550° F (290° C.) at an absolute pressure of about 0.2 mm Hg to about 5 mm Hg to remove the bulk of the unwanted materials.

(b) High temperature steam distillation comprises deaerating the polyol polyester to a level of less than about 0.10% by volume of dissolved oxygen, heating the deaerated oil to a temperature between about 390° F. (200° C.) to about 480° F. (250° C.), and stripping the oil at an absolute pressure of less than about 15 mm Hg for a period of from about 5 seconds to about 15 minutes using a medium such as steam, nitrogen, or an inert gas in an amount from about 0.2% to about 20% by weight of the polyester. Stripping at very high temperatures for short residence times minimizes the content of undesirable materials.

In the presently disclosed process, high temperature steam distillation is preferably used as the sole finishing step.

The finished polyol fatty acid polyester may be further treated with color removing adsorbent such as silica gel and subsequently deodorized if needed.

D. Addition of Alkaline Material

The key step of the present invention is the addition of an alkaline material to the crude polyol fatty acid polyester at a point after the synthesis, but prior to the finishing of the crude polyol fatty acid polyester as disclosed above. The addition of alkaline materials at this time retards or prevents the formation of pro-oxidants during these the finishing steps.

The alkaline materials are added in an amount sufficient to adjust the pH of the final product (or polyester) to from about 6.0 to about 8.5, preferably to from about 6.5 to about 7.5, and most preferably to about 7.0. The alkaline materials used herein include, for example, base solutions, alkaline silica gels, alkaline bleaching clays, and mixtures thereof. When the alkaline material is alkaline silica gel, or alkaline bleaching clay, it is permissible to use these materials in the drying/and or absorptive bleaching refining operations steps disclosed above. Their substitution does not detrimentally affect the removal of the soap and or residual color bodies in the crude product. Such alkaline silica and clays include, for example, Try Syl, manufactured by W. R. Grace, P.O. Box 2117, Baltimore, Md.; and Pure-flo, manufactured by Oil Dri Corporation of America, 520 North Michigan Avenue, Chicago, Ill.

In the present invention, it is preferred that the alkaline material used be a base solution. The base solution used in the present invention comprises a base material dissolved in an organic solvent. This base solution is added just prior to the initiation of the finishing steps as described above. For example, when thermal evaporation is used the base is added prior to that step. If only high temperature steam distillation is used, the base solution is added just before that step. Regardless of when the base solution is added, it is preferred that the resulting mixture of the base solution and crude product be maintained at a temperature from about 70° F. (21° C.) to about 140° F. (60° C.), preferably from about 90° F. (32° C.) to about 120° F. (49° C.) for from about 5 to about 30 minutes before the finishing step or steps are commenced.

The following is a detailed description of the base solution used in the present invention:

1. Base

Bases useful in the present invention are selected from the group consisting of hydroxides, carbonates, and oxide salts of alkali metals, and alkaline earth metals. The alkali metals and alkaline earth metals useful herein are selected from the group consisting of lithium, sodium, potassium, magnesium, calcium, barium, and mixtures thereof. Preferred alkali metals and alkaline earth metals are selected from the group consisting of potassium, sodium, calcium and mixtures thereof. Most preferred is potassium.

In the present invention, the most preferred bases are selected from the group consisting of potassium hydroxide, potassium carbonate, sodium hydroxide, and mixtures thereof.

The amount of base used in the base solution of the present invention may vary greatly depending upon how much of the polyol fatty acid polyester is present and how quickly one wishes to reach the required pH for said polyester. For example, when there is a small amount of polyol fatty acid polyester present, it is recommended that a base solution with a low concentration of base be used since the final pH may be easily overshot with even a small amount of a stronger base solution. On the other hand, with a large amount of polyol fatty acid polyester, a higher concentration of base in the base solution would be desirable so that the pH level can be reached fairly quickly. Base solutions having varying concentrations of alkaline materials may also be used herein to have better control of the alkalinization of the crude polyol fatty acid polyester.

(b) Organic Solvents

The bases disclosed above are dissolved in an organic solvent in order to form the base solution used as the alkaline material. These organic solvents are selected from material routinely used in industrial chemical processes as disclosed in Erickson, D. R., World Conference Proceedings, "Edible Fats and Oils Processing", *Journal of American Oil Chemists Soc.*, 1990. The sol vents useful herein are selected from the group of organic solvents consisting of alcohols, ethers, and mixtures thereof. The organic solvents in the present invention are typically used at levels from about 0.01% to about 3% of the weight of the crude polyol polyester present.

(1) Alcohols

Alcohols useful as an organic solvent in the present invention are selected from the group consisting of organic mono- and polyhydric alcohols.

The monohydric alcohols useful herein are selected from the group consisting of primary, secondary and tertiary alcohols.

Monohydric alcohols useful herein are selected from the group consisting of methyl, ethyl, propyl, isopropyl, butyl, isobutyl, sec butyl, pentyl, isopentyl, tert-pentyl, heptyl, octyl, benzyl, phenylethyl alcohols, and mixtures thereof, i.e. $C_1$ to $C_{10}$ monohydric alcohols. Preferred are primary monohydric alcohols selected from the group consisting of methyl, ethyl, and propyl alcohols. Most preferred is methyl alcohol.

Polyhydric alcohols useful in the present invention are not limited necessarily by the number of hydroxyl groups they contain. Rather, the polyhydric alcohols useful herein are limited by their ability to adequately solvate the base selected for use. Polyhydric alcohols used in making the base solutions of the present invention, preferably have up to about 3 hydroxyl groups. Such alcohols are selected from the group consisting of ethylene glycol, propylene glycol, glycerol, and mixtures thereof. Most preferred is propylene glycol.

(2) Ethers

Ethers useful as an organic solvent in the present invention are selected from the group consisting of ethyl ether, propyl ether, isopropyl ether, butyl ether, and mixtures thereof. The most preferred ethers are those selected from the group consisting of ethyl ether, isopropyl ether, and mixtures thereof.

The following examples exemplify the present invention. All percentages, parts and ratios herein are by weight unless otherwise specified.

EXAMPLE I

Methyl esters of a fully hydrogenated (Iodine Value about 1) soy oil (about 90.9 kg), about 20 kg of potassium hydroxide pellets, and about 273 kg of methanol are mixed in a stainless steel batch reactor. This mixture is then heated to about 145° F. (63° C.) with agitation for about 1 to 3 hours at atmospheric pressure (1 mm Hg). During this time, a portion of the methyl esters are saponified forming soap.

An additional about 594.5 kg of methyl esters of a partially hydrogenated cottonseed oil with an Iodine Value of about 93, is then added to the soap mixture. The methyl esters are prepared by distillation under vacuum without fractionation. Granular sucrose (about 136.4 kg) is added to the soap/ester mixture to give an about 5:1 molar ratio of ester to sucrose. Granular potassium s carbonate is then added to the mixture (~0.5% of the reaction mix) to catalyze the transesterification. This mixture is agitated and slowly heated at atmospheric pressure until the temperature reaches about 225° F. (107° C.). This is to remove the methanol. A vacuum is then pulled and the mixture agitated for up to about 4 hours to form the mono-, di-, and triesters. Small quantities of tetra- and pentaesters are also formed during this stage. Additional methyl ester (about 950 kg) is added to bring and maintain the molar ratio of the esters to sucrose to about 12:1. Additional potassium carbonate is then added to the mixture (~0.5% is of the initial reaction mix). When the reaction conditions stabilize at about 275° F. (135° C.), a nitrogen sparge is used to improve agitation and promote methanol stripping. This second reaction stage lasts approximately 4 to 16 hours.

The reaction mixture is then cooled under nitrogen to between about 149° F. (65° C.) and about 185° F. (85° C.). The crude reaction mixture is agitated with between about 0.25% and about 6% water. The hydrated crude reaction mixture is passed through a centrifuge to separate a heavy and a light phase. The heavy phase which contains the soaps, excess sugars, and potassium carbonate is discarded.

The light phase which contains methyl esters and the sucrose polyester (SPE) is then washed with distilled water (about 286 kg) having a pH of about 5 to about 8 and a temperature of about 160° F. (71° C.) to about 200° F. (93° C.). After removal of the separated water phase, the light phase is dried at a temperature 160° F (71° C.) to about 200F. (93° C.) under about 70 mm Hg or less vacuum for about 30 to 60 minutes. About 0.5–3% of Filtrol™ 105, an absorbing clay (made by Engelhardt Corp. Catalyst and Chemicals Div. Jackson, Miss.) is added and the mix is agitated at about 167° F. (75° C.) to about 200° F. (93° C.). The slurry is separated by filtration or other means until there is less than 0.1% fines. The liquid is then passed through a 1 micron filter.

The refined and bleached reaction mix is then cooled to about 120° F. (49° C.). A base solution comprising about 3.2 kg propylene glycol and about 0.033 kg of potassium hydroxide is then added to bring the reaction mix's initial pH of about 4.4 up to about 7.2. The refined and bleached reaction mix undergoes thermal evaporation by passing the mixture through a stainless steel wiped-film evaporator or other suitable equipment to removed the bulk of the methyl esters.. The liquid is thermally evaporated at about 392° F. (200° C.) to about 455° F. (235° C.) under no greater than about 1 mm Hg of vacuum.

The SPE is then steam stripped by passing it downwardly through a stainless steel packed column or other suitable device at from about 392° F. (200° C.) to about 482° F. (250° C.) under a vacuum of about 5 mm Hg or less. The lower than normal processing temperatures herein minimize formation of undesirable materials.

Steam is introduced to the bottom of the column and passes counter-currently to the sucrose polyester. Feed rates and temperature are adjusted until the methyl ester content of the SPE is below 1000 ppm. The mixture is then cooled to between about 130° F. (54.5° C.) and about 185° F. (85° C.) and passed through an about 1 micron filter.

The oxidative stability of the SPE is measured using a modified Active Oxygen Method (AOM) which measures an increase in peroxide value (AOCS Method Cd 8–53) over time while sparging air through the sample at about 208° F. (about 98° C.). The AOM is a standard method used in the fats and oils industry to measure oxidative stability of triglyceride (AOCS Method Cd 12–57). This method has been modified for ease of application in the time frame of 0–2 hr. where oxidation impact on flavor is especially important. The method used to measure stability is described as follows:

1. Charge 300 gm of sample into a clean, dry glass flask, and begin purging the sample with dry nitrogen.

2. Heat the flask to about 208° F. (98° C.) using a heating mantle connected to a thermo watch to control temperature.

3. After temperature is reached, collect a baseline sample for time zero reference and analyze for ppm peroxide. Switch from nitrogen to dry air at about 8.57 cc/min./ml of sample.

4. Collect samples at intervals of 20 to 40 min. and analyze for ppm peroxide.

The following shows the effect of base addition as disclosed by the present application upon the oxidative stability of SPE. All SPEs, treated and untreated, were synthesized from identical raw materials and process conditions except for the base addition step.

TABLE 1

Effect of Base Addition on SPE Oxidative Stability

| Time (Min.) | Peroxide Value (ppm) | |
|---|---|---|
| | Base Added SPE | Non-Base Added SPE |
| 0 | 23 | 34 |
| 20 | 27 | 117 |
| 40 | 31 | 331 |
| 60 | 43 | 479 |
| 90 | 67 | 861 |
| 120 | 162 | 1503 |

The untreated SPEs have consistently higher peroxide levels indicating reduced oxidative stability.

EXAMPLE 2

The SPE crude is prepared in the same manner as Example 1 except that more methanol is added during the initial soap generation step (325.5 kg versus 273 kg).

After refining and bleaching as disclosed in Example 1, the SPE crude is cooled to a temperature of about 120° F. (49° C.) and a base solution of 22.5 kg of methanol and 0.23 kg of potassium hydroxide is added to bring the reaction mix's initial pH of about 4.4 up to a pH of about 7.0. The bulk of the methyl ester is distilled off during finishing and the remaining liquid SPE is deodorized; both steps done as disclosed in Example 1.

The oxidative stability is measured using the AOM as disclosed in Example 1.

TABLE 2

Effect of Base Addition on SPE Oxidative Stability

| Time (min) | SPE Peroxide Value (ppm) |
|---|---|
| 0 | 4 |
| 20 | 11 |
| 40 | 37 |
| 60 | 41 |
| 90 | 122 |
| 120 | 366 |

Although the peroxide values are somewhat higher than the base treated SPEs of Example 1, they are significantly lower than the untreated samples in Example 1.

EXAMPLE 3

SPE is prepared as disclosed in Example 1 and divided into approximately two equal fractions. Each fraction is then refined, bleached, and distilled as disclosed in Example 1, except on a laboratory scale.

Wash fraction 1 with a 1N sodium hydroxide solution, having a pH of about 14, using an amount equal to about 10% of the weight of the crude SPE. Heat the solution to a temperature of about 180° F. (82° C.), and maintain this temperature for about 15 minutes. Separate the water phase and add the Filtrol-105 to the liquid crude SPE at a level of about 1% by weight of the crude SPE. Filter out the sediment and distill the liquid at about 410° F. (210° C.) at about 1 mm Hg to remove the methyl ester.

Wash fraction 2 with deionized water, having a pH of about 7.2, in an amount equal to about 15% by weight of the crude SPE. Heat the solution to a temperature of about 180° F. (82° C.), and maintain this temperature for about 15 minutes. Separate the water phase and add the Filtrol-105 to the liquid crude SPE at a level of about 1% by weight of the crude SPE. Filter out the sediment, and add about 0.06 weight percent of propylene glycol and potassium hydroxide, containing about 0.06 weight percent of potassium hydroxide. Maintain the solution temperature at about 120° F. (49° C.). Distill the solution at a temperature of about 410° F. (210° C.) at about 1 mm Hg.

Oxidative stability of the SPE fractions are measured using the AOM disclosed in Example 1.

TABLE 3

Effect of Base Addition v. Alkaline Water Washing on Oxidative Stability

| | Peroxide Value (ppm) | |
|---|---|---|
| Time (min.) | Fraction 1 (Alkaline Water Wash) | Fraction 2 (Base Addition) |
| 0 | 135 | 14 |
| 20 | 330 | 45 |
| 40 | 623 | 203 |
| 90 | 1117 | 250 |
| 120 | 1196 | 377 |

EXAMPLE 4

Prepare, refine, and bleach crude SPE as in Example 1. Divide the crude into four equal fractions. Add to two of the fractions a sufficient amount of propylene glycol potassium hydroxide solution to yield a pH of 6.5 and 8.3. Add to a third fraction propylene glycol citric acid solution such that its pH is 4.5. Add nothing to the last fraction; its pH is about 5.6. All pH is measured in a 10% solution of SPE in neutral deionized water and isopropanol at 110°–120° F. Subject the four SPE fractions, having differing pH levels, to thermal evaporation, as disclosed in Example 1. The oxidative stability of each fraction is measured using AOM as disclosed in Example 1.

The Figure included herein graphically illustrates comparative oxidative stability of the four fractions. The Figure shows that the oxidative stability, as predicted using AOM, of the base added fractions is superior.

What is claimed is:

1. A process for making polyol fatty acid polyesters having improved oxidative stability, which process comprises the steps of:
   A. heating a mixture of a polyol, a fatty acid ester, an emulsifier and a catalyst to form a reaction mixture;
   B. adding to the reaction mixture more fatty acid ester to form a crude polyol fatty acid polyester;
   C. refining the crude polyol fatty acid polyester;
   D. adding an alkaline material to the crude polyol fatty acid polyester in an amount such that the final product has a pH of from about 6.5 to about 8.5; and
   E. finishing the crude polyol fatty acid polyester by heating the crude to a temperature ranging from about 190° C. to about 290° C.;
   F. isolating the polyol fatty acid polyester of step E.

2. A process according to claim 1 wherein the alkaline material is selected from the group consisting of a base solution, alkaline silica gel, alkaline clay, and combinations thereof.

3. A process according to claim 1 wherein the final product's pH is from about 6.5 to about 7.5.

4. A process according to claim 3 wherein the final product's pH is about 7.0.

5. A process according to claim 1 wherein the polyol fatty acid polyester is a sucrose fatty acid polyester.

6. A product prepared by the process of claim 1.

7. A process for making polyol fatty acid polyesters having improved oxidative stability, which process comprises the steps of:
   A. heating a mixture of a polyol, a fatty acid ester, an alkali metal fatty acid soap and a catalyst to a temperature of from about 194° F. (90° C.) to about 325° F. (163° C.), at a pressure of from about 0.1 mm Hg to about 760 mm Hg to form a reaction mixture;
   B. adding to the reaction mixture more fatty acid ester to form a crude polyol fatty acid polyester;
   C. refining the crude polyol fatty acid polyester;
   D. adding a base solution to the crude polyol fatty acid polyester in an amount such that the final product has a pH ranging from about 6.5 to about 8.5; and
   E. finishing the crude polyol fatty acid polyester by heating the crude to a temperature ranging from about 190° C. to about 290° C.;
   F. isolating the polyol fatty acid polyester of step E.

8. A process according to claim 7 wherein the crude polyol fatty acid polyester is finished in step E via thermal evaporation.

9. A process according to claim 7 wherein the crude polyol fatty acid polyester is finished in step E via a high temperature steam distillation.

10. A process according to claim 9 wherein the oxygen level during the finishing step is less than 0.1%.

11. A process according to claim 10 wherein the final product's pH is from about 6.5 to about 7.5.

12. A process according to claim 11 wherein the final product's pH is about 7.0.

13. A process according to claim 10 wherein the polyol fatty acid polyester is a sucrose fatty acid polyester.

14. A process according to claim 10 wherein, after the addition of the base solution, the resulting mixture is maintained at a temperature from about 70° F. (21° C.) to about 140° F. (60° C.) from about 5 to about 30 minutes.

15. A process according to claim 14 wherein the resulting mixture is maintained at a temperature from about 90° F. (32° C.) to about 120° F. (49° C.) for about 5 to about 30 minutes.

16. A process according to claim 10 wherein the base solution comprises:
   (a) a base selected from the group consisting of alkali metal and alkaline earth metal hydroxides, carbonates, oxides, and mixtures thereof; and
   (b) an organic solvent selected from the group consisting of alcohols, ethers, and mixtures thereof.

17. A process according to claim 16 wherein the alkali metals and alkaline earth metals are selected from the group consisting of lithium, sodium, potassium, magnesium, calcium, barium, and mixtures thereof.

18. A process according to claim 17 wherein the alkali metals and alkaline earth metals are selected from the group consisting of potassium, sodium, calcium and mixtures thereof.

19. A process according to claim 18 wherein the alkali metal is potassium.

20. A process according to claim 16 wherein the organic solvent is an alcohol selected from the group consisting of monohydric, polyhydric, and mixtures of mono- and polyhydric alcohols.

21. A process according to claim 20 wherein the alcohol is a $C_1$ to $C_{10}$ monohydric alcohol.

22. The process according to claim 21 wherein the monohydric alcohols are selected from the group consisting of methyl, ethyl, propyl, isopropyl, butyl, isobutyl, sec butyl, pentyl, isopentyl, tert-pentyl, heptyl, octyl, benzyl, phenylethyl alcohols, and mixtures thereof.

23. A process according to claim 22 wherein the alcohol is selected from the group consisting of methyl, ethyl, and propyl alcohols.

24. A process according to claim 23 wherein the alcohol is methyl alcohol.

25. A process according to claim 20 wherein the organic solvent is selected from the group consisting of ethylene glycol, propylene glycol, glycerol and mixtures thereof.

26. A process according to claim 25 wherein the solvent is propylene glycol.

27. A process according to claim 16 wherein the organic solvent is selected from the group consisting of ethyl ether, propyl ether, isopropyl ether, butyl ether, and mixtures thereof.

28. A process according to claim 27 wherein the organic solvent is selected from the group consisting of ethyl ether, propyl ether, and mixtures thereof.

29. A process according to claim 28 wherein the organic solvent is ethyl ether.

* * * * *